(12) United States Patent
Ciccolo et al.

(10) Patent No.: US 6,614,348 B2
(45) Date of Patent: Sep. 2, 2003

(54) SYSTEM AND METHOD FOR MONITORING BEHAVIOR PATTERNS

(75) Inventors: Arthur C. Ciccolo, Ridgefield, CT (US); Phillip Hobbs, Briarcliff Manor, NY (US); John D. Mackay, Sleepy Hollow, NY (US); Howard E. Sachar, Mount Kisco, NY (US)

(73) Assignee: International Business Machines Corporation, Armonk, NY (US)

( * ) Notice: Subject to any disclaimer, the term of this patent is extended or adjusted under 35 U.S.C. 154(b) by 181 days.

(21) Appl. No.: 09/814,785

(22) Filed: Mar. 23, 2001

(65) Prior Publication Data

US 2002/0135484 A1 Sep. 26, 2002

(51) Int. Cl.$^7$ ................................................ G08B 13/00
(52) U.S. Cl. ...................... 340/541; 340/565; 340/573.4
(58) Field of Search ................................ 340/555, 565, 340/545.3, 556, 557, 573.3, 573.4, 541, 576, 575; 128/903; 600/529, 543, 558, 595; 250/338.5, 339.02, 339.05, 339.14

(56) References Cited

U.S. PATENT DOCUMENTS

| | | | | |
|---|---|---|---|---|
| 4,777,477 A | | 10/1988 | Watson | 340/573.4 |
| 4,839,631 A | * | 6/1989 | Tsuji | 340/541 |
| 5,841,137 A | * | 11/1998 | Whitney | 250/338.5 |
| 5,942,976 A | | 8/1999 | Wieser et al. | 340/565 |
| 5,998,780 A | | 12/1999 | Kramer | 340/555 |
| 6,028,514 A | * | 2/2000 | Lemelson et al. | 340/573.1 |
| 6,043,493 A | | 3/2000 | Kim et al. | 250/349 |
| 6,054,928 A | * | 4/2000 | Lemelson et al. | 340/573.4 |
| 6,384,414 B1 | * | 5/2002 | Fisher et al. | 340/567 |
| 6,437,696 B1 | * | 8/2002 | Lemelson et al. | 340/573.4 |

* cited by examiner

*Primary Examiner*—Van Trieu
(74) *Attorney, Agent, or Firm*—Stephen C. Kaufman, Esq.; McGinn & Gibb, PLLC

(57) ABSTRACT

A system and method for monitoring behavior patterns which effectively distinguishes between alarming and non-alarming behavior patterns, includes at least one sensor for detecting behavior patterns, a memory device coupled to the sensor, for storing standard behavior patterns, and a processor, coupled to the memory device, for comparing standard behavior patterns with detected behavior patterns, and causing a response to be activated when standard behavior patterns and detected behavior patterns have a predetermined relationship.

29 Claims, 6 Drawing Sheets

SYSTEM AND METHOD FOR MONITORING BEHAVIOR PATTERNS

BACKGROUND OF THE INVENTION

1. Field of the Invention

The present invention generally relates to a monitoring system and, more particularly, a system for monitoring behavior patterns of individuals and other animated objects which effectively distinguishes between alarming and non-alarming patterns.

2. Description of the Related Art

As shown in FIG. 1, conventional monitoring systems are often audiovisual systems 100 that employ audio and video equipment to monitor individuals. In such systems, microphones 101 and cameras 102 are used to detect behavior patterns (e.g., a monitored person lying in a bed between 10:00 p.m. and 7:00 a. m., showering between 7:30 a.m. and 8:00 a.m., etc) as they occur. Signals representing such patterns are transmitted from the microphones and cameras to a video display 103 and speakers 104 which are monitored continuously by a human monitor 105. When the human monitor 105 observes an alarming behavior pattern (e.g., the monitored person lying on the floor, the monitored person not in bed at midnight, etc.), the human monitor may take corrective action (e.g., tend to an elderly person whose behavior patterns are being monitored) or report such alarming pattern to the appropriate person or agency (e.g. a nurse who can tend to such elderly person).

However, such audiovisual systems are intrusive, inefficient and costly. For example, a video signal requires substantial bandwidth making it burdensome and costly to transmit. Further, the use of a human monitor is costly and subject to human error. Human monitors must be trained and must remain in close proximity to the monitored individual. In the case of video observation, the low rate of alarming events (visual changes in the scene) often lead to poor attention by support people and the possibility of ignoring an alarming event. Therefore, if the human monitor is not active and vigilant, an alarming pattern can be easily overlooked. Furthermore, such systems are unnecessarily intrusive into the lives of the persons being monitored because the human monitor's observations are not limited to just alarming behavior patterns, but must include each and every action of the person being monitored.

Other conventional monitoring systems include motion sensing systems which use motion sensors to detect movement in a space being monitored. Motion sensors are typically photosensors that detect moving objects based on discrete approximations of space or time. In such systems, the sensors are connected to an alarm circuit which typically has an audible alarm. However, such motion sensing monitoring systems monitor only a predefined space, not monitor behavior patterns of individuals. This severely limits the utility of such systems. Further, Generally, such systems do not distinguish between motion caused by a person and motion from any other entity of comparable size or with a comparable extent of motion. In addition, such systems do not distinguish between a monitored individual and a non-monitored individual. In either case, regardless of whether the individual detected is monitored or non-monitored, if such a system is active and functioning properly, then it will alarm upon the individual entering the space.

Therefore, motion sensing systems do not detect alarming behavior patterns. For example, such systems cannot monitor elderly individuals with alzheimer's disease to detect when such individuals are not in bed at a certain hour or are lying on the floor of their room, etc. Similarly, such systems cannot monitor infants to detect when such infants are not in their cribs, or are near dangerous objects such as windows or appliances, etc. Nor can such systems monitor warehouses or retail shopping areas to detect behavior patterns that would indicate theft.

Another conventional system is an infrared monitoring system which uses infrared sensors to monitor spaces such as museums and banks. Infrared sensors operate based on Stefan-Boltzmann's law that every body radiates an energy proportional to a fourth power of an absolute temperature of the body. Such sensors typically detect radiant energy emitted from bodies, human or otherwise, within a wavelength range from approximately 6 to 15 micrometers.

A monitoring system utilizing infrared sensors is disclosed, for example, in Weiser et al. (U.S. Pat. No. 5,942,976). Infrared sensors used in such systems include a housing with an entrance window which is transparent to the infrared radiation, focusing optics, one or more infrared sensors, and an electrical signal evaluation circuit. Such systems further include an alarm circuit which typically has an audible alarm.

With such a system, if an intruder enters the space monitored by the infrared detector, his infrared body radiation enters through the entrance window into the detector and is focused by the focusing optics onto the infrared sensors. The infrared sensors output a signal to the circuit which amplifies the signal and compares it to a predetermined threshold. If the threshold is exceeded, then an intrusion alarm signal is generated.

However, infrared systems also have their shortcomings. For example, like other monitoring systems, existing infrared systems either detect an alarming event or they don't. These systems typically provide no additional information (e.g., duration, specific location, frequency of occurrence, etc.) about the event. In other words, these systems have no ability to interpret a pattern of behavior and select from a variety of potential responses.

In addition, conventional infrared systems, similar to motion sensing systems, monitor only a predefined space, not behavior patterns of individuals. Thus, like motion sensing systems, such infrared systems are limited in utility. For example, such systems cannot distinguish between a monitored individual and a non-monitored individual. In either case, regardless of whether the individual is monitored, if such a system is active and functioning properly, it will alarm upon the individual entering the space. Furthermore, because conventional infrared systems have simple and nondiscriminating detectors, the systems often detect events that aren't actually alarming and are, therefore, result in a high false/positive response rate.

Therefore, as with other systems, conventional infrared systems cannot effectively monitor behavior patterns and detect alarming behavior patterns that would indicate, for example, theft in a warehouse or retail store, or a potential harm to an infant or an alzheimer's patient.

SUMMARY OF THE INVENTION

In view of the foregoing and other problems, it is, therefore, an object of the present invention to provide a system and method for monitoring behavior patterns of individuals which effectively distinguishes between alarming and non-alarming behavior patterns.

In a first aspect, a system for monitoring behavior patterns includes sensors for detecting behavior patterns, a memory device for storing behavior patterns, a processor for comparing detected behavior patterns with standard behavior patterns and activating a response when the detected behavior pattern and at least one standard behavior pattern have a predetermined relationship, such as when the detected data matches the stored data, or which the detected data differs from stored data.

The system may include a plurality of sensors which are interconnected and the sensors may be infrared sensors for detecting infrared radiation. For example, the infrared sensor may detect a variation in radiant energy of less than one Kelvin. The system may use the multiple sensors to detect behavior patterns comprised of sequences of patterns, compare the detected behavior patterns to the standard behavior patterns, generate a signal to activate additional sensors to detect supplementary data, and transmit this supplementary data to a remote location.

The memory device may be a conventional semiconductor memory device. Further, the processor may be an adaptive processor programmed with a learning algorithm so that the system "learns" new standard behavior patterns while it operates and "forgets" old standard behavior patterns that may no longer be considered alarming.

The response activated may also include additional sensors for collecting additional information. The response may also include a human response, an audiovisual or photographic device or an auto-dialer which makes a call to the police, ambulance, etc.

In a second embodiment, a method of monitoring behavior patterns includes storing standard behavior patterns, detecting behavior patterns, comparing detected behavior patterns to standard behavior patterns, and activating a response when a detected behavior pattern and at least one standard behavior pattern have a predetermined relationship, such as when the detected data matches the standard data, or which the detected data differs from standard data.

The inventive method may also employ multiple sensors to detect behavior patterns comprised of sequences of patterns, compare the detected behavior pattern data to the standard behavior patterns, and activate a response that may include additional sensors to detect supplementary data, and transmit this supplementary data a remote location.

With the novel features of the claimed invention, the behavior patterns of individuals can be monitored with an improved ability to distinguish between alarming and non-alarming behavior patterns. In addition, based on the behavior pattern detected, the claimed invention may initiate a variety of responses, such as the collection of additional data from a plurality of heterogeneous sensors. Moreover, the system at the device level and at the aggregation of devices level, can discover patterns that should be categorized as alarming (or normal) and incrementally alter what conditions precipitate the transmission of an alarm or other information.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF THE PREFERRED EMBODIMENT OF THE INVENTION

Figure 1:
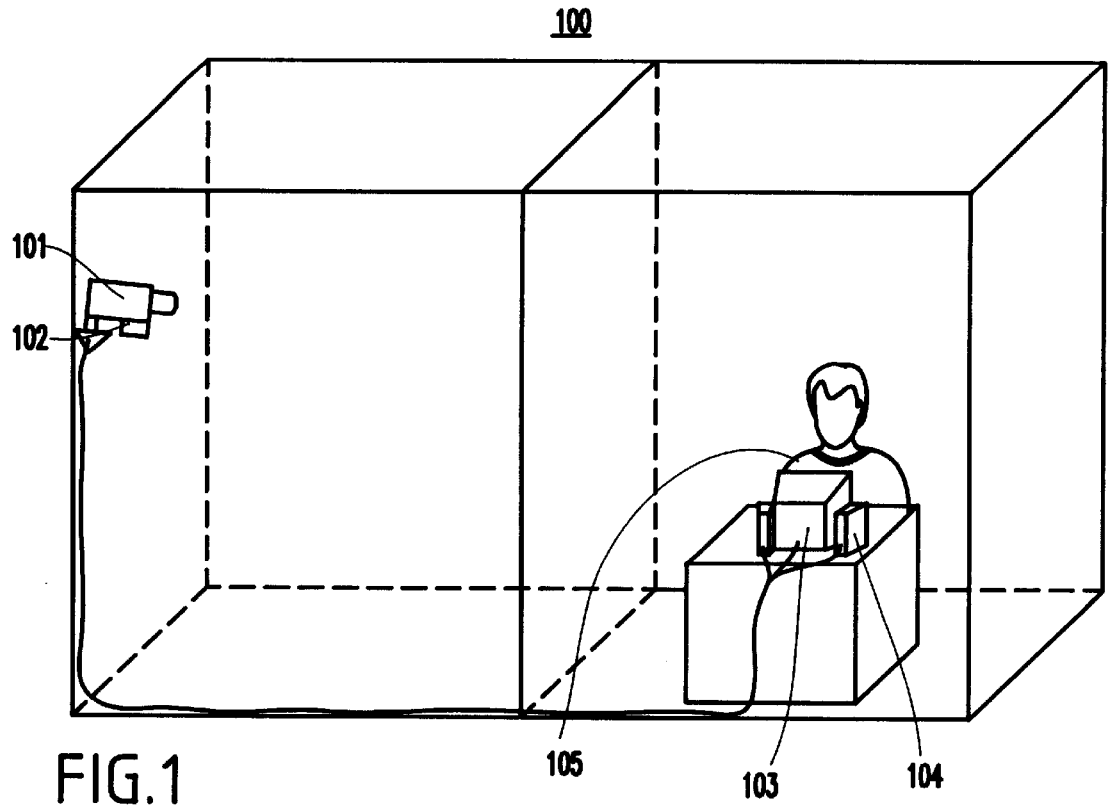
FIG. 1 illustrates a conventional monitoring system 100 using audio/video equipment.
Figure 2A:
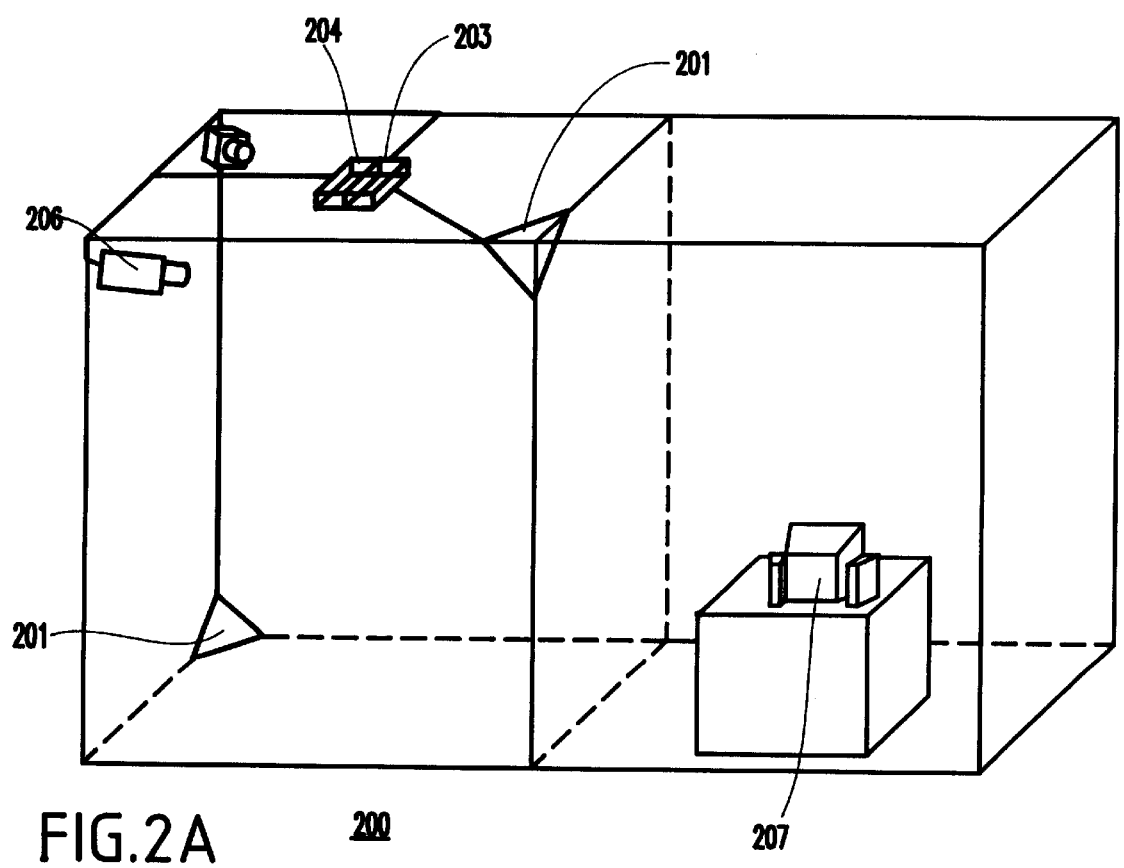
FIG. 2A illustrates a monitoring system 200 according to a preferred embodiment of the present invention.

Referring now to the drawings, FIG. 2A illustrates a monitoring system according to a preferred embodiment of present invention.

In a preferred embodiment, a monitoring system 200 includes one or more sensors 201 for detecting radiant energy levels which define behavior patterns of monitored objects. The sensors 201 transmit data when there is a change in the field of view of the sensors 201. Such sensors may be, for example, infrared sensors. Further, the sensors 201 may be inexpensive and highly sensitive, and may be located at any location that is not prominent and allow the sensors 201 to operate without interference, such as the ceiling or wall of a room. In addition, since only alarms and/or small amounts of image data are sent, little bandwidth and therefore, little wiring is needed.

In addition, the sensors 201 are easy to install and are programmed so that they understand the geography of the space within which they operate. The highly sensitive sensors 201 also allow the inventive system 200 to efficiently monitor a large space. For example, if each pixel in a sensor 201 provides one byte of data and images one square foot of area in the monitored field, and the embodied array is 8 feet×12 feet, a complete representation of the monitored field is under 100 bytes, uncompressed. Moreover, depending on the granularity of the data required, the area covered by one pixel can be adjusted by remotely adjusting the lens.

As further shown in FIG. 2A, the inventive system 200 includes a memory device 203 connected to the sensors 201. The memory device 203 may be a conventional memory device (e.g., random access memory (RAM)) and is used to store information, including standard behavior patterns which are defined by radiant energy level data. For example, if the system 200 is being used to monitor an alzheimer's patient, the standard behavior pattern stored in the memory device 203 may be defined by radiant energy level data corresponding to the patient's energy level existing at a certain location at a certain hour.

Figure 2B:
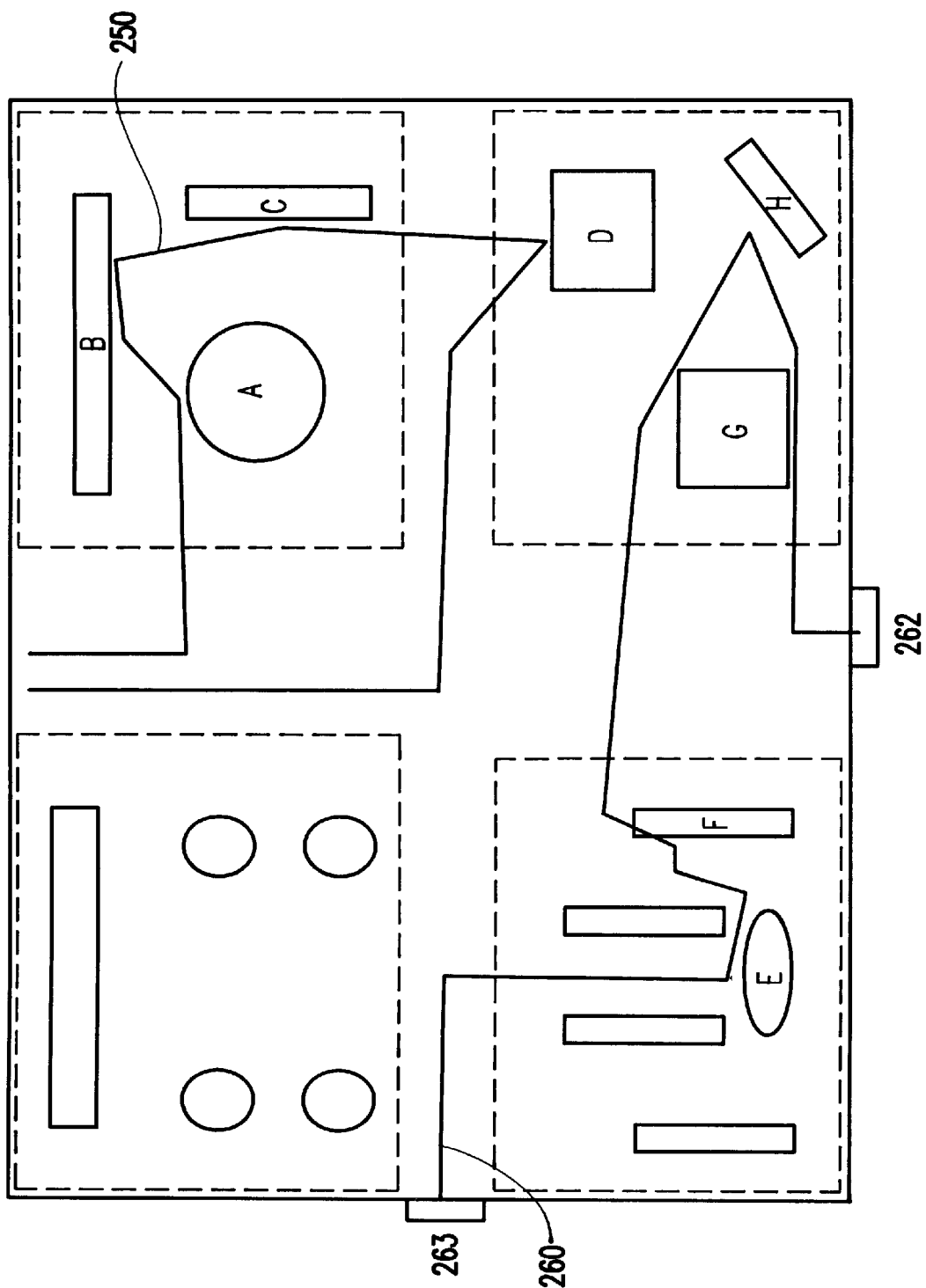
FIG. 2B illustrates exemplary behavior patterns that may be detected by the system 200.

FIG. 2B illustrates two exemplary behavior patterns 250, 260 which are defined by radiant energy levels. As shown in FIG. 2B, a first behavior pattern 250 is defined by radiant energy level data corresponding to an individual entering a door 251, dwelling for a certain time period at points A, B, C and D, then exiting door 251. Similarly, a second behavior pattern 260 is defined by radiant energy level data corresponding to an individual entering a door 262, dwelling for a certain time period at points E, F, G and H, then exiting door 263.

Any behavior pattern which can be defined by radiant energy level data can be stored in the memory device. For example, an employee moving repeatedly between a locker room and a work station may be a behavior pattern indicating a theft by the employee. Radiant energy level data defining this behavior pattern may be stored in the memory device 203 as a standard behavior pattern. Similarly, a retail store customer making repeated movements into and out of a handbag or an individual moving repeatedly into and out of the store without making a purchase, may be a behavior pattern indicating shoplifting. In that case, radiant energy level data defining such a suspicious behavior pattern may be stored in the memory device 203 as a standard behavior pattern.

The system further includes a processor 204 which is coupled to the sensors 201 and to the memory device 203 and which compares detected behavior patterns with the standard behavior patterns which are stored in the memory device 203. The processor 204 may be a conventional microprocessor. When it is determined by the processor 204 that the detected behavior patterns and the standard behavior patterns have a predetermined relationship (e.g., the detected data matches the standard data or the detected data differs from the standard data), the processor 204 may cause an alarm signal to be generated.

Further, when he processor 204 finds a predetermined relationship exists between a detected behavior pattern and a standard behavior pattern, the processor causes a response 206 to be activated. The response 206 shown in FIG. 2A is an audiovisual system, however, the inventive system may include any variety of responses 206. For example, the response 206 may include a human response or an audible alarm such as a siren or a visual alarm such as flashing lights. In addition, the response 206 may include other data capture devices such as a camera for taking still photographs or an audiovisual display that can be observed by a human monitor. The response 206 may also include an auto-dialer for automatically dialing the police, ambulance or fire department.

In addition, the inventive system 200 may include a variety of potential responses 206, and may activate a particular response 206 based on the standard behavior pattern for which a predetermined relationship is identified. For example, if the system is being used in a retail store, and the standard behavior pattern includes an individual entering and leaving the store three times in the same day without making a purchase which would indicate shoplifting, the response 206 activated may include an audiovisual system which follows the individual throughout the store the next time he enters. On the other hand, if the standard behavior pattern includes an intense heat in the store indicating a fire, the response 206 activated may include an automatic phone call to the fire department. The particular response 206 to be activated may be stored in the memory device 203.

The inventive system 200 may also store in the memory device 203, information regarding the a history of detected behavior patterns, predetermined relationships identified, responses activated and other important information such as the date, time and comments from a human monitor regarding a response 206 activated.

The inventive system 200 may include a controller 207 for controlling the system 200. The controller 207 may be hardwired to the system or may be wirelessly connected to the system 200. For example, the controller 207 may be a personal computer and include a keyboard for inputting and modifying data (e.g., standard behavior patterns, predetermined relationship which causes an alarm signal to be generated, and the type of response activated) to the memory device 203. The controller 207 may include a video display unit for visually displaying data stored on the memory device 203. The controller 207 may also be used for such functions as activating and deactivating the system 200 and controlling the functions of the processor 204 such as overriding the response activated (e.g., turning off an audible alarm or audiovisual system).

Figure 2C:
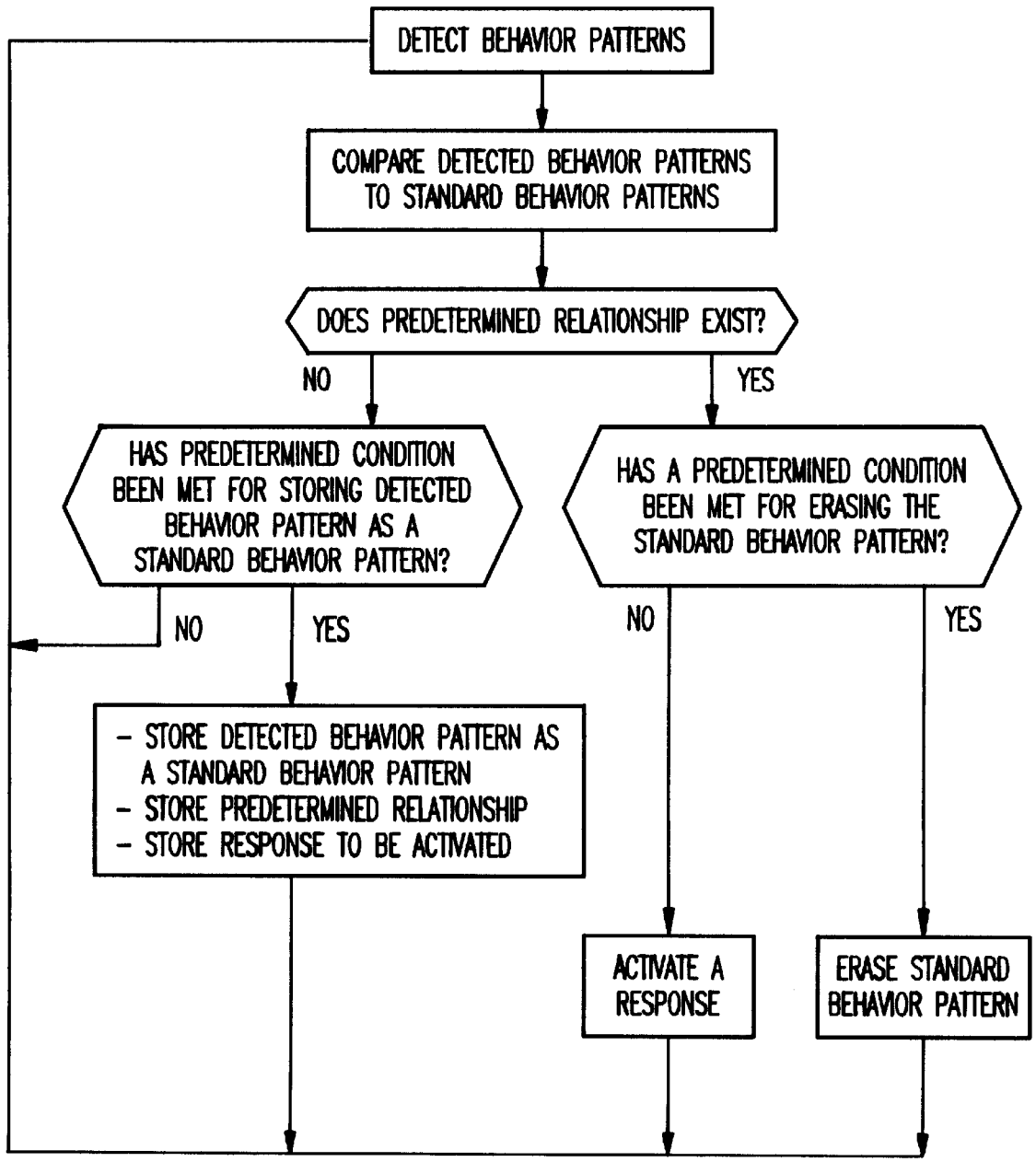
FIG. 2C illustrates a learning algorithm that may be used by the processor 204 to automatically store new standard behavior patterns and erase existing standard behavior patterns.

Further, the processor 204 of the inventive monitoring system may include a learning function so that it can "learn" new standard behavior patterns and erase (i.e., "forget") old behavior patterns from the list of standard behavior patterns in the memory device. FIG. 2C shows a learning algorithm 270 that may be used by the processor 204. As shown in FIG. 2C, after the system determines that no predetermined relationship exists, the processor 204 may determine if certain predetermined conditions have been met for storing the detected behavior pattern as a new standard behavior pattern. For instance, the predetermined condition may be that the detected behavior pattern has been detected n times over a time period t. If the processor 204 determines that this condition has been not been met, the algorithm returns the system 200 back to detecting behavior patterns. However, if this predetermined condition in the learning algorithm 270 is met, the processor 204 causes the detected behavior pattern to be automatically stored in the memory device as a new standard behavior pattern, and automatically causes to be stored a preternimed relationship corresponding to the new standard behavior pattern and a response to be activated when the predetermined relationship exists.

On the other hand, if the processor 204 determines that a predetermined relationship does exist, the processor may then determine if a predetermined condition has been met for erasing the standard behavior pattern having a predetermined relationship with the detected behavior pattern. For instance, such a predetermined condition may be that the system 200 has detected this particular predetermined relationship x times over a time period t. If the processor 204 determines that the predetermined condition has not been met, the processor 204 proceeds to cause an alarm signal to be generated. On the other hand, if the predetermined condition has been met, the processor 204 causes the corresponding standard behavior pattern to be erased from the memory device 203.

Figure 3:
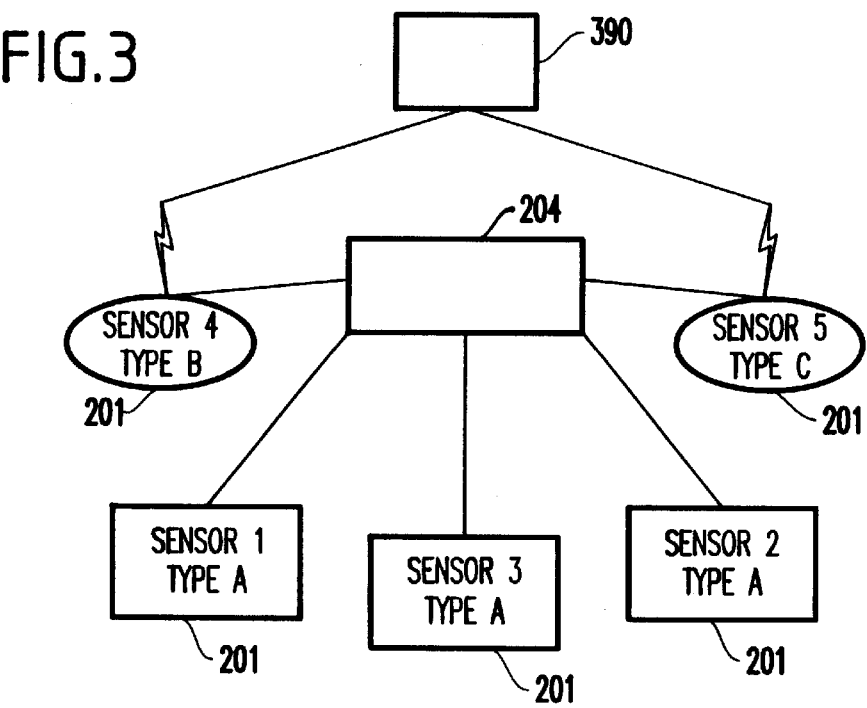
FIG. 3 illustrates a monitoring system 200 having multiple sensors, according to an aspect of a preferred embodiment of the present invention.

Furthermore, as shown in FIG. 3, the inventive system 200 may include a plurality of sensors 201 coupled to the processor 204. The sensors 201 may have varying specifications as shown in FIG. 3. The sensors 201 may work together to detect behavior patterns comprised of sequences of patterns and the processor 204 compares the behavior patterns detected by the plurality of sensors to the standard behavior patterns stored in the memory device 203. If a predetermined relationship is found, the response 206 activated may include additional sensors 201 to detect supplementary data which may be wirelessly transmitted to a remote location 390 (e.g. the controller 207) to be analyzed.

The inventive monitoring system 200 also provides an effective and efficient system of monitoring the behavior patterns 202 of individuals such as hospital patients, infants, retail customers, employees and prisoners. The sensors 201 can detect whether an individual whose behavior patterns are being monitored has an elevated or depressed body temperature. The system may also detect alarming events surrounding such a monitored individual such as fire, low/high temperature, smoke, etc. and whether windows or doors are open or closed. Thus, there may be no need for attendants or continuous live video or audio. Therefore, the system saves money and is not subject to human error like the audiovisual monitoring system. In addition, this system is not intrusive like conventional audiovisual systems because the behavior patterns of the individuals being monitored are not continuously monitored by another person. Further, unlike motion sensor and conventional infrared sensor monitoring systems, the inventive system is able to distinguish between a monitored individual and a non-monitored individual by comparing each individual's behavior patterns to predetermined patterns. Moreover, the system requires no more for installation than a smoke detector and has a short calibration procedure.

Figure 4A:
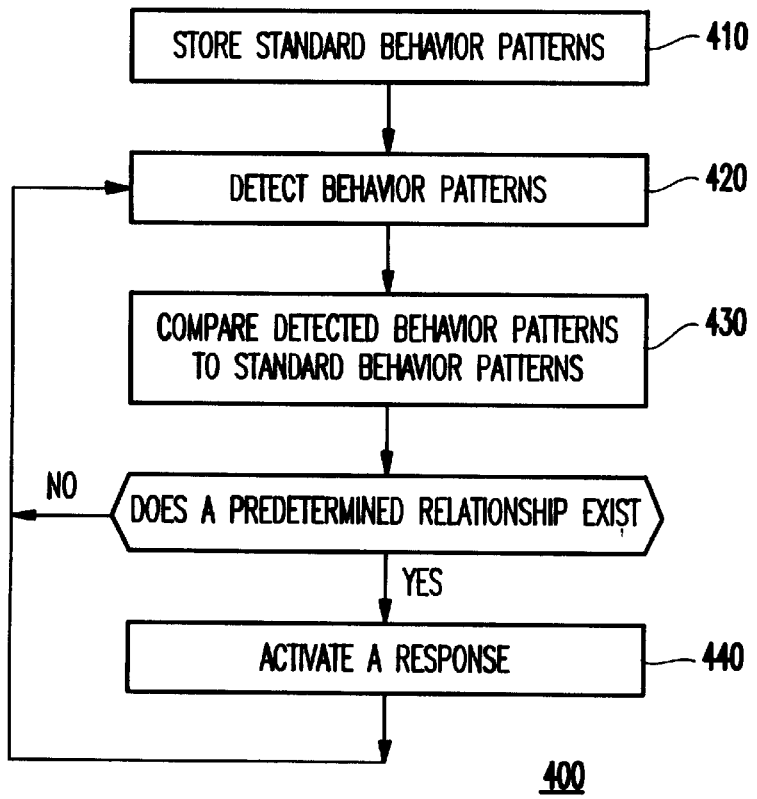
FIG. 4A is a flow chart illustrating a method for monitoring behavior patterns according to a second embodiment of the present invention.

FIG. 4 provides a flow chart illustrating a method 400 for monitoring behavior patterns according to a second embodiment of the present invention.

According to the claimed method 400 of monitoring behavior patterns 202 (see, also, FIGS. 2C and 3), standard behavior patterns are stored (410). This may be performed by a memory device such as a semiconductor memory device or, more specifically, a conventional semiconductor RAM. As explained above, the standard behavior patterns may be defined by radiant energy level data.

The inventive method 400 further includes detecting (420) behavior patterns by detecting radiant energies. As explained above, this may be performed by more than one sensor 201 such as infrared sensors.

The inventive method 400 further includes comparing (430) detected behavior patterns with standard behavior patterns which are stored. This may be performed by a processor as explained above. If no predetermined relationship between the detected behavior pattern and the standard behavior patterns is found, no response is activated. If such a predetermined relationship is found, a response is activated (440). As explained above, the response may include a human response, an audiovisual or still photographic capture device or to an auto-dialer which causes a telephone call to be initiated to the proper authorities.

Furthermore, the inventive method 400 may use the multiple sensors 201 coupled to a processor 204. The sensors 201 may have varying specifications as shown in FIG. 3. The sensors 201 may work together to detect behavior patterns comprised of sequences of patterns and the processor 204 compares the detected behavior patterns to the standard behavior patterns. The processor 204 may then generate a signal to activate additional sensors 201 to detect supplementary data, and transmit this supplementary data a remote location 390.

Figure 4B:
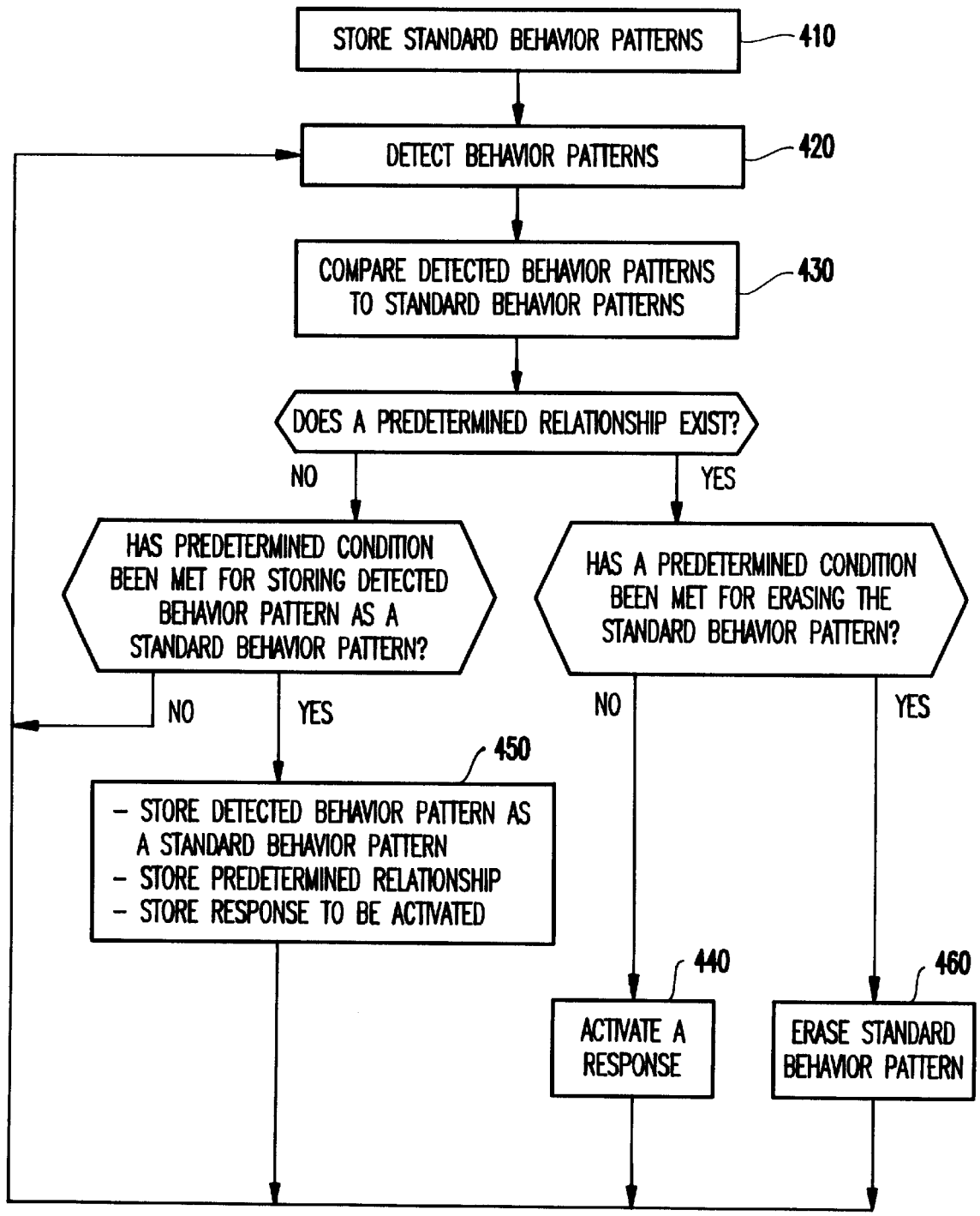
FIG. 4B is a flow chart illustrating a method for monitoring behavior patterns which includes a learning algorithm, according to a second embodiment of the present invention.

In addition, the claimed method 400 may include a learning algorithm (e.g., see FIG. 2C) so as to include "learning" new standard behavior patterns and erasing (i.e., forgetting) old behavior patterns from the list of standard behavior patterns in the memory device. As shown in FIG. 4B, after it is determined that no predetermined relationship exists, it is determined if certain predetermined conditions have been met for storing the detected behavior pattern as a new standard behavior pattern. If it is determined that this condition has been not been met, the method 400 returns to detecting behavior patterns (420). However, if this predetermined condition is met, the detected behavior pattern is automatically stored (450) as a new standard behavior pattern, and a pretermined relationship corresponding to the new standard behavior pattern and a response to be activated when the predetermined relationship exists, are also automatically stored (450).

On the other hand, if it is determined that a predetermined relationship does exist, it is then determined if a predetermined condition has been met for erasing the standard behavior pattern having a predetermined relationship with the detected behavior pattern. If it is determined that the predetermined condition has not been met, a response is then activated (440). On the other hand, if the predetermined condition has been met, the corresponding standard behavior pattern is erased from the memory device (460).

Figure 5:
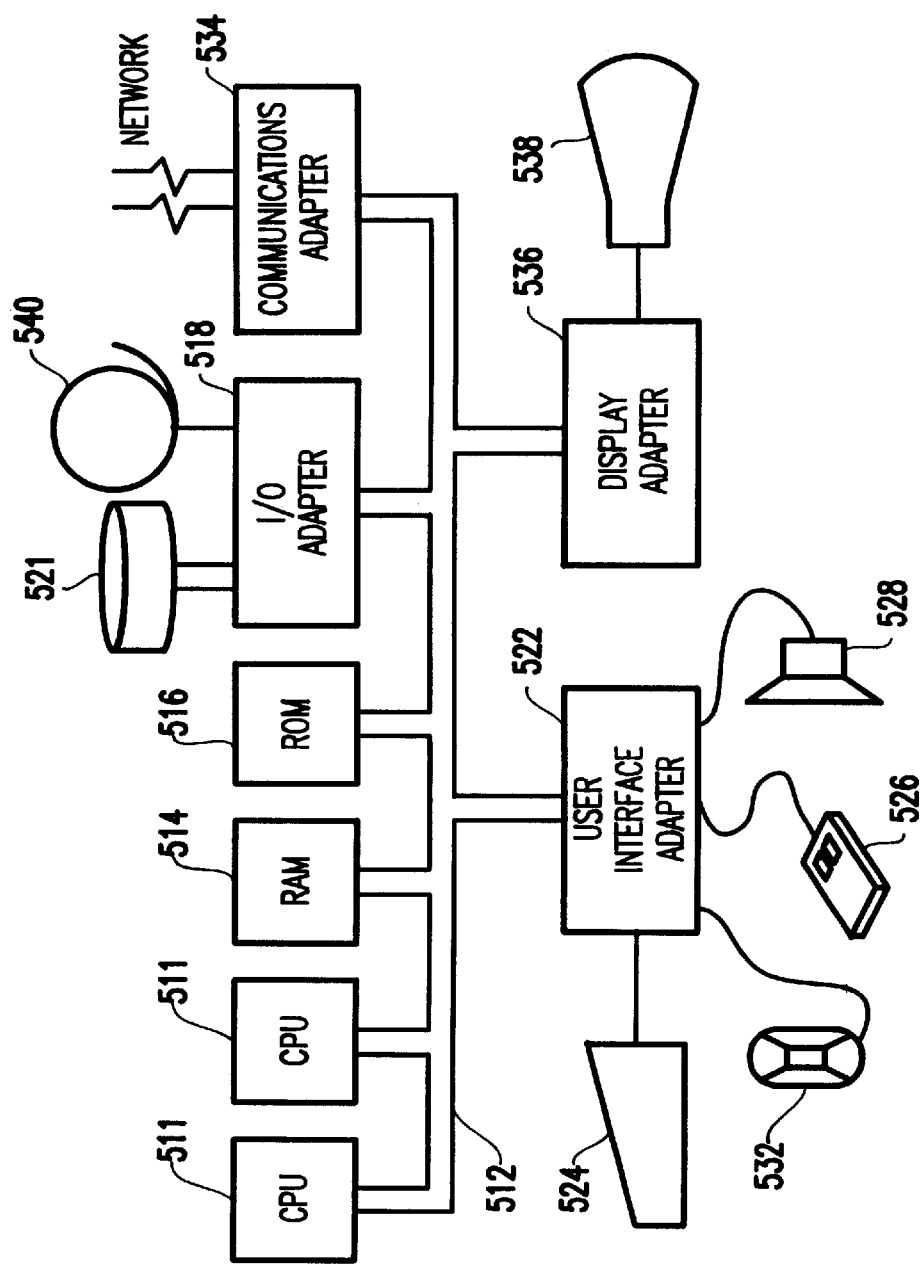
FIG. 5 illustrates an hardware/information handling system 500 for incorporating the present invention.

FIG. 5 illustrates a typical hardware configuration of an information handling/computer system in accordance with the invention and which preferably has at least one processor or central processing unit (CPU) 511.

The CPUs 511 are interconnected via a system bus 512 to a random access memory (RAM) 514, read-only memory (ROM) 516, input/output (I/O) adapter 518 (for connecting peripheral devices such as disk units 521 and tape drives 540 to the bus 512), user interface adapter 522 (for connecting a keyboard 524, mouse 526, speaker 528, microphone 532, and/or other user interface device to the bus 512), a communication adapter 534 for connecting an information handling system to a data processing network, the Internet, an Intranet, a personal area network (PAN), etc., and a display adapter 536 for connecting the bus 512 to a display device 538 and/or printer 539 (e.g., a digital printer or the like).

In addition to the hardware/software environment described above, a different aspect of the invention includes a computer-implemented method for performing the above method. As an example, this method may be implemented in the particular environment discussed above.

Such a method may be implemented, for example, by operating a computer, as embodied by a digital data processing apparatus, to execute a sequence of machine-readable instructions. These instructions may reside in various types of signal-bearing media.

Thus, this aspect of the present invention is directed to a programmed product, comprising signal-bearing media tangibly embodying a program of machine-readable instructions executable by a digital data processor incorporating the CPU 511 and hardware above, to perform the method of the invention.

Figure 6:
FIG. 6 illustrates a signal bearing medium 600 (i.e., storage medium) for storing steps of a program of a method according to the present invention.

This signal-bearing media may include, for example, a RAM contained within the CPU 511, as represented by the fast-access storage for example. Alternatively, the instructions may be contained in another signal-bearing media, such as a magnetic data storage diskette 600 (FIG. 6), directly or indirectly accessible by the CPU 511.

Whether contained in the diskette 600, the computer/CPU 511, or elsewhere, the instructions may be stored on a variety of machine-readable data storage media, such as DASD storage (e.g., a conventional "hard drive" or a RAID array), magnetic tape, electronic read-only memory (e.g., ROM, EPROM, or EEPROM), an optical storage device (e.g. CD-ROM, WORM, DVD, digital optical tape, etc.), paper "punch" cards, or other suitable signal-bearing media including transmission media such as digital and analog and communication links and wireless. In an illustrative embodiment of the invention, the machine-readable instructions may comprise software object code, compiled from a language such as "C", etc.

With the novel features of the claimed invention, the behavior patterns of individuals can be monitored with an improved ability to distinguish between alarming and non-alarming behavior patterns. In addition, based on the behavior pattern detected, the claimed invention may initiate a variety of responses, such as the collection of additional data from a plurality of heterogeneous sensors. Moreover, the system at the device level and at the aggregation of devices level, can discover patterns that should be categorized as alarming (or normal) and incrementally alter what conditions precipitate the transmission of an alarm or other information.

While a preferred embodiment of the present invention has been described above, it should be understood that it has been provided as an example only. Thus, those skilled in the art will recognize that the invention can be practiced with modification within the spirit and scope of the appended claims.

What we claim is:

1. A system for monitoring behavior patterns, comprising:
   at least one sensor for detecting behavior patterns;
   a memory device coupled to said at least one sensor, for storing standard behavior patterns; and
   a processor, coupled to said memory device, for comparing said standard behavior patterns with detected behavior patterns, and causing a response to be activated when at least one standard behavior pattern and said detected behavior pattern have a predetermined relationship,
   wherein said standard behavior patterns and said detected behavior patterns comprise radiant energy level data.

2. The system according to claim 1, wherein said predetermined relationship comprises said detected behavior pattern matching said at least one standard behavior pattern.

3. The system according to claim 1, wherein said predetermined relationship comprises said detected behavior pattern differing from said at least one standard behavior pattern.

4. The system according to claim 1, wherein said sensor comprises an infrared sensor.

5. The system according to claim 4, wherein said infrared sensor detects a variation in radiant energy of less than one Kelvin.

6. The system according to claim 1, wherein said behavior patterns comprise behavior patterns of one of either infants, hospital patients, employees, customers and prisoners.

7. The system according to claim 1, further comprising a controller having a video display unit for controlling said system including activating and deactivating said system, inputting data to said memory device, reading data from said memory device, updating data in said memory device and inputting predetermined relationship data and response data.

8. The system according to claim 1, wherein said response comprises one of a human response, an audiovisual device, a photographic device and an auto-dialer for automatically dialing a telephone.

9. The system according to claim 1, wherein said at least one sensor comprises a plurality of sensors, and
   wherein said plurality of sensors are interconnected.

10. The system according to claim 9, wherein said plurality of sensors detects behavior patterns comprised of sequences of patterns, and
    wherein said response comprises activating additional sensors to detect supplementary data which is transmitted to a remote location.

11. The system according to claim 1, wherein said processor comprises a microprocessor.

12. The system according to claim 1, wherein said processor comprises an adaptive processor such that when a predetermined condition is met, said processor automatically stores a detected behavior pattern as a new standard behavior pattern, and automatically stores a predetermined relationship corresponding to said new standard behavior pattern which causes a response to be activated, and automatically stores a response to be activated when said predetermined relationship exists.

13. The system according to claim 1, wherein said processor comprises an adaptive processor such that when a predetermined condition is met, said processor automatically erases a standard behavior pattern from said memory device.

14. The system according to claim 1, wherein said system monitors said behavior patterns without human intervention.

15. The system according to claim 1, wherein said memory device stores information other than detected behavior patterns from said at least one sensor.

16. A method of monitoring behavior patterns, comprising:
    storing standard behavior patterns;
    using at least one sensor to detect behavior patterns;
    comparing detected behavior patterns to said standard behavior patterns; and
    activating a response when a detected behavior pattern and at least one standard behavior pattern have a predetermined relationship,
    wherein said standard behavior patterns and said detected behavior patterns comprise radiant energy level data.

17. The method according to claim 16, wherein said predetermined relationship comprises said detected behavior pattern matching said at least one standard behavior pattern.

18. The method according to claim 16, wherein said predetermined relationship comprises said detected behavior pattern differing from said at least one standard behavior pattern.

19. The method according to claim 16, wherein said sensor comprises an infrared sensor.

20. The method according to claim 19, wherein said infrared sensor detects a variation in radiant energy of less than one Kelvin.

21. The method according to claim 16, wherein said at least one sensor comprises a plurality of sensors, and
    wherein said plurality of sensors are interconnected.

22. The method according to claim 21, wherein said plurality of sensors detect behavior patterns comprised of sequences of patterns, and
    wherein said response comprises activating additional sensors to detect supplementary data which is transmitted to a remote location.

23. The method according to claim 16, wherein said standard behavior patterns are stored in a semiconductor memory device.

24. The method according to claim 16, wherein said behavior patterns comprise behavior patterns of infants, hospital patients, employees, customers and prisoners.

25. The method according to claim 16, wherein said response comprises one of a human response, an audiovisual device, a photographic device and an auto-dialer for automatically dialing a telephone.

26. The method according to claim 16, wherein said comparing is performed by a processor.

27. The method according to claim 16, further comprising:
    determining whether a predetermined condition has been met for storing detected behavior pattern as a standard behavior pattern;

when it is determined predetermine that a predetermined condition has been met for storing detected behavior pattern as a standard behavior pattern, storing said detected behavior patterns as new standard behavior patterns, predetermined relationships corresponding to said new standard behavior patterns and responses to be activated;

determining whether a predetermined condition has been met for erasing a standard behavior pattern; and when it is detemined that a predetermined condition has been met for erasing a standard behavior pattern, erasing said standard behavior pattern.

28. The method according to claim 16, wherein when a predetermined relationship exists, it is determined whether a predetermined condition has been met for erasing a standard behavior pattern, and when a predetermined relationship does not exist, it is determined whether a predetermined condition has been met for storing a detected behavior pattern as a standard behavior pattern.

29. A signal bearing medium tangibly embodying a program of machine readable instructions executable by a digital processing apparatus to perform a method for monitoring behavior patterns, said method comprising:

storing standard behavior patterns;

using at least one sensor to detect behavior patterns;

comparing detected behavior patterns to said standard behavior patterns, and activating a response when said detected behavior pattern and at least one standard behavior pattern have a predetermined relationship, wherein said standard behavior patterns and said detected behavior patterns comprise radiant energy level data.

* * * * *

Disclaimer 6,614,348 — Arthur C. Ciccolo, Ridgefield, CT. (US); Phillip Hobbs, Briarcliff Manor, NY; (US); John D. Mackay, Sleepy Hollow, NY (US); Howard E. Sachar, Mount Kisco, NY (US). SYSTEM AND METHOD FOR MONITORING BEHAVIOR PATTERNS. Patent dated Sep. 2, 2003. Disclaimer filed Oct. 4, 2006 by the assignee, International Business Machines Corporation.

Hereby enters this disclaimer to all claims of said patent.

*(Official Gazette February 27, 2007)*